US007977659B2

(12) United States Patent
Harper et al.

(10) Patent No.: US 7,977,659 B2
(45) Date of Patent: Jul. 12, 2011

(54) RADIO FREQUENCY SCREEN ASSEMBLY FOR MICROWAVE CAVITIES

(75) Inventors: Curt Harper, Frederick, MD (US); George Jarrard, Westminster, MD (US); Kevin Lascola, Columbia, MD (US); Matthew Schroeder, Mt. Airy, MD (US); David A. Sprankle, Hagerstown, MD (US); Charles H. Wood, Rockville, MD (US)

(73) Assignee: Fusion UV Systems, Inc., Gaithersburg, MD (US)

( * ) Notice: Subject to any disclaimer, the term of this patent is extended or adjusted under 35 U.S.C. 154(b) by 399 days.

(21) Appl. No.: 12/149,446

(22) Filed: May 1, 2008

(65) Prior Publication Data

US 2009/0273937 A1 Nov. 5, 2009

(51) Int. Cl.
*G21G 4/00* (2006.01)
*H05B 41/16* (2006.01)
*A61N 5/06* (2006.01)

(52) U.S. Cl. .............. 250/504 R; 250/492.1; 250/493.1; 250/494.1

(58) Field of Classification Search .................. 362/341, 362/386, 364, 368; 250/492.1, 493.1, 494.1, 250/504 R
See application file for complete search history.

(56) References Cited

U.S. PATENT DOCUMENTS 6,841,790 B1 * 1/2005 Phillips et al. ............ 250/504 R

* cited by examiner

*Primary Examiner* — John A Ward

(74) *Attorney, Agent, or Firm* — McDermott Will & Emery LLP

(57) ABSTRACT

A luminaire assembly comprising at least one magnetron, a least one microwave-powered bulb, a luminaire reflector, at least one waveguide, and a radio-frequency screen assembly is provided. The radio-frequency screen assembly, the radio frequency gasket, and the luminaire reflector are configured to form a microwave cavity that can accommodate a microwave-powered bulb. The at least one waveguide is configured to couple energy from the at least one magnetron to the microwave-powered bulb. The radio-frequency screen accommodates at least one latching structure. The at least one latching structure is configured to sufficiently compress or to release the radio-frequency screen and the luminaire assembly. In another embodiment, a radio-frequency screen assembly comprises a frame which comprises an opening defined by a plurality of edges. The frame comprises a planar portion and further comprises a ridge at one of the edges that extends in a direction perpendicular to the planar portion.

15 Claims, 11 Drawing Sheets

RADIO FREQUENCY SCREEN ASSEMBLY FOR MICROWAVE CAVITIES

RELATED APPLICATION

This application is related to a U.S. patent application Ser. No. 12/149,447, entitled "Bonded Single-Piece Ultra-Violet Lamp Luminaire for Microwave Cavities," filed concurrently herewith, which is fully incorporated herein by reference.

DESCRIPTION OF THE INVENTION

1. Field of the Invention

An invention consistent with this disclosure relates to the sealing a microwave cavity, such as that used in connection with an ultraviolet lamp.

2. Background of the Invention

Ultraviolet (UV) curing systems are in wide use. Among other uses, UV curing systems utilize UV radiation to cure adhesives and inks. UV curing presents a number of benefits over alternative curing methods. For example, UV curing may reduce costs, increase throughput, and provide a higher quality finished product.

Microwave-powered UV lamps, or luminaires, may be used in the UV curing process to generate the required UV radiation. A deconstructed view of a conventional prior art microwave-powered UV lamp can be seen in FIG. 1.

Luminaire assembly 10, depicted in FIG. 1, comprises one or more magnetrons (not shown) and waveguides (not shown) encased in luminaire assembly housing 20. Luminaire assembly 10 further comprises luminaire reflector assembly 30. Luminaire reflector assembly 30 comprises main reflector 36, microwave coupling slot 35, two or more end reflector bulbs supports 32 and two or more end reflectors 34. The luminaire assembly may further comprise a centering spring plate for insertion of microwave-powered bulb 50 into end reflector bulb support 32 after luminaire reflector assembly 30 has been affixed into luminaire housing 20. Luminaire assembly 10 further comprises a curved end reflector groove to support the end reflector 32. Luminaire assembly 10 may further comprise curved gaskets to electrically connect the waveguide to the luminaire reflector.

Luminaire reflector assembly 30 is configured to be mated to radio-frequency (RF) screen assembly 40. Another view of prior art RF screen assembly 40 is shown in FIG. 2. RF screen assembly 40 comprises RF screen frame 44, RF screen wire mesh material 46, RF screen gasket 42 (FIG. 2) and screw openings 38. The embodiment depicted in FIGS. 1 and 2 corresponds, for example, to a ten inch luminaire, which conventionally uses 8 screws to seal the microwave cavity.

In the luminaire assembly depicted in FIG. 1, the luminaire reflector assembly 30 and the radio-frequency (RF) screen assembly 40 form the walls of a microwave cavity that can accommodate a microwave-powered bulb 50. Depicted in FIG. 1 and FIG. 2, the RF screen assembly 40 comprises RF screen frame 44, RF screen mesh material 46, and RF screen gasket 42. Microwave-powered bulb 50 produced radiation which exits the luminaire through RF screen wire mesh material 46. The RF screen wire mesh material is generally woven with very fine tungsten wire with a wire diameter of only 0.002 inch. The spacing between the wires is such that the mesh is 90% open and allows about 90% of the UV energy to exit the cavity. The spacing is still small enough that the microwave energy is contained within the microwave cavity. While this design allows maximum operating efficiency the mesh material is mechanically fragile mechanically and easily damaged by accidental contact.

In the luminaire assembly, the luminaire reflector assembly 30 and the RF screen mesh material 46 require direct electrical connection. For example, poor contact between these two components or an air gap will result in dielectric breakdown, which in turn can damage components. In addition, any gap between the luminaire reflector assembly 30 and the RF screen mesh material 46 may allow microwave energy to escape the cavity, which could cause interference with other electronic equipment. Therefore, it is preferable that the sub assemblies that make up the microwave cavity exhibit a sufficiently tight seal.

As shown in FIG. 1 and FIG. 2, conventional prior art microwave cavities provide the tight seal through the use of screws 28 and screw openings 38 in RF screen frame 44, as well as through the use of an RF screen gasket 42. To maintain a sufficiently tight seal, existing luminaires typically require the use of between 4-8 screws 28 with corresponding screw openings 38, depending upon the dimensions of the luminaire. For example, exemplary conventional luminaires with RF screen assemblies measuring approximately ten inches by six inches use 8 screws for compressive force. Luminaires with RF screen assemblies measuring approximately 6 inches by 6 inches conventionally use 4 screws for compressive force. The screws 28 and the screw openings 38 attach the RF screen assembly 40 to the luminaire reflector assembly 30 and supply the necessary compressive force to ensure that the microwave cavity is sufficiently sealed.

This prior art configuration presents a problem. When there is a need to open the cavity—to, for example, change a burned out bulb—all the screws must be removed. Opening and resealing the cavity requires a tool (typically a screwdriver). Further, the time necessary to open and reseal the cavity represents a cost. Moreover, existing commercial latches that are available generally cannot be utilized on conventional microwave lamps because of space constraints. For example, it is desirable that latches not extend past the screen frame more than about 1/10 of an inch. If latches extend further than about 1/10 of an inch, the latches would be vulnerable to damage. In addition, if the latches extend beyond the screen frame then the latches could damage other components of a system. Further, it is desirable that latches not protrude over the RF screen mesh material 46. Additionally, a receptacle component for existing commercial latches would conventionally require space on the back side of the reflector assembly. This space is typically not available in luminaire assembly housing 20.

It is accordingly an object of the invention to make it easier and/or faster to remove and reinstall an RF screen in the field. The present invention solves the aforementioned problems.

It is another object of the present invention to reduce the possibility of cross-threading screws into screw holes.

It is another object of the present invention to retain a screw or a fastener with the screen assembly. Retaining a screw or a fastener with the screen assembly will ensure that the screw or the fastener does not get dropped or misplaced, thereby saving time, effort, and expense.

Additionally, in the prior art design a screwdriver can slip off a screw-head and damage the fragile RF screen mesh material 46. Accordingly, it is another object of the present invention to reduce the risk of damage to RF screen mesh material 46.

SUMMARY OF THE INVENTION

An invention consistent with the present disclosure relates to an improved sealing of the microwave cavity in UV lamps, or any microwave cavity. The present invention provides for a luminaire assembly comprising a luminaire assembly housing, a luminaire reflector assembly, a microwave-powered bulb, and an RF screen assembly. In accordance with the present invention, the RF screen assembly is attached to the luminaire reflector assembly in a manner improved over the prior art. The present invention provides for quick release fastener for the RF screen assembly.

The present invention also provides for the luminaire assembly as discussed above where the quick release fastener is a hook-shaped latch. The hook-shaped latch comprises a substantially hook-shaped region that is configured to pass through and opening in the RF screen assembly to couple the RF screen assembly to the luminaire reflector assembly. The hook-shaped latch may be used to quickly attach and detach the RF screen assembly from the reflector assembly.

The present invention also provides for the luminaire assembly as discussed above where the luminaire reflector is configured with at least one latching post. The at least one latching post is configured to extend through at least one opening in the RF screen assembly. The at least one latching post is configured to couple with a latching structure. The latching structure is configured to couple the RF screen assembly and the luminaire reflector assembly.

The present invention also provides for the luminaire assembly as discussed above where the luminaire reflector is configured with at least one latching post. The at least one latching post is configured to couple with at least one latching structure with a wedge-shaped region. The latching structure couples with the latching post to couple the RF screen assembly and the luminaire reflector assembly.

The present invention also provides for the luminaire assembly as discussed above where the luminaire assembly further comprises a cam lock rail and at least one cam lock. The at least one cam lock in combination with the cam lock rail is configured to couple the RF screen assembly and the luminaire reflector assembly.

The present invention also provides for the luminaire assembly as discussed above where the quick release fastener is a captive fast lead screw. The captive fast lead screw is used to quickly attach and detach the RF screen assembly from the luminaire reflector assembly.

The present invention also provides for the luminaire assembly as discussed above where the luminaire reflector is configured with at least one latching post. The at least one latching post is configured to couple with at least one latching structure preferably comprising Tinnerman™ spring clips, or equivalents, that are used the secure the RF screen assembly to the luminaire reflector assembly.

The present invention also provides for an RF screen assembly comprising an RF screen frame, an RF screen gasket, and an RF screen mesh material. Any one of the aforementioned embodiments of the present invention can be used to secure the RF screen assembly to the luminaire reflector assembly to ensure compression of the gasket. In one embodiment, an RF screen frame defines a plane. The RF screen frame comprises a metal ridge along one or more sides of an inside opening of the RF screen frame. The metal ridge extends in a direction perpendicular to the plane. The metal ridge can prevent a tool, such as a screwdriver, from slipping off the frame into the RF screen mesh material. Further, the metal ridge can provide additional structural strength to the RF screen frame.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the present embodiments (exemplary embodiments) of the invention, examples of which are illustrated in the accompanying drawings. Wherever possible, the same reference numbers will be used throughout the drawings to refer to the same or like parts.

Figure 1:
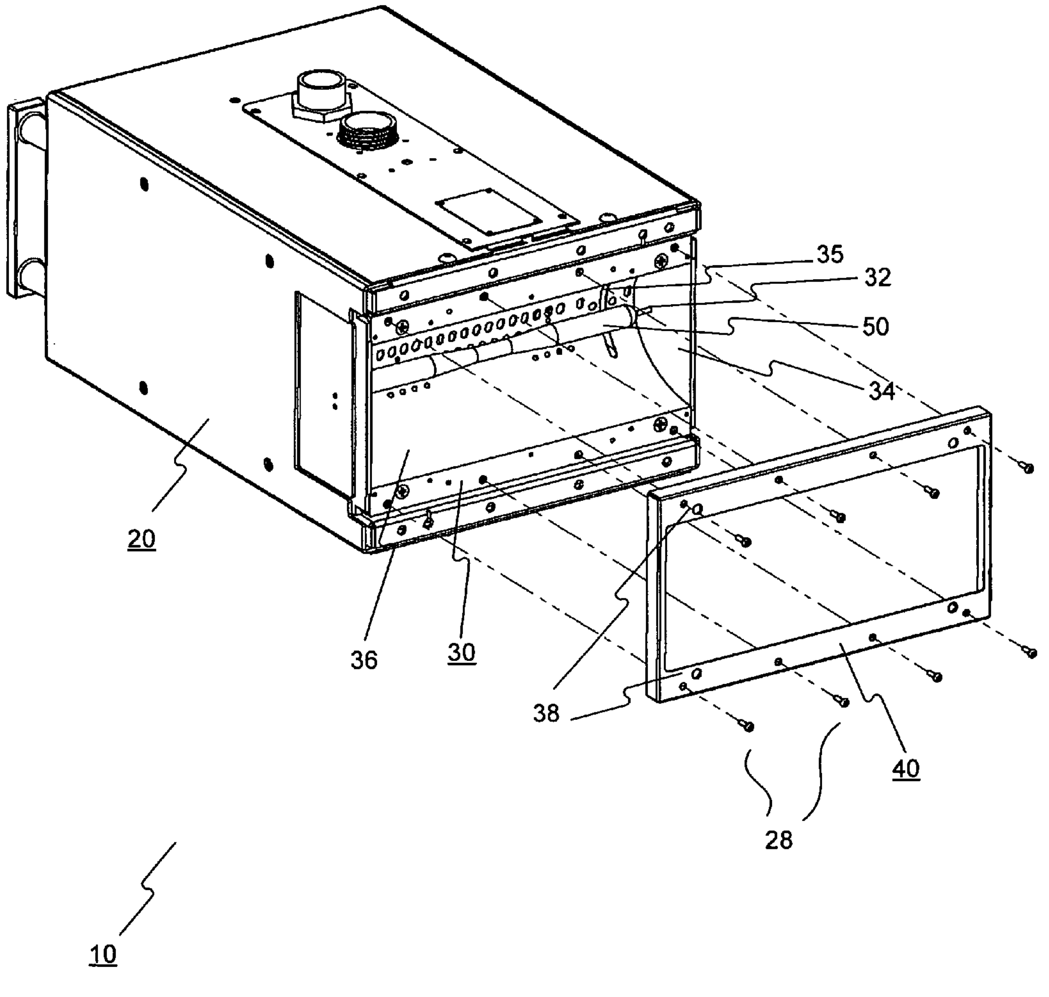
FIG. 1 (PRIOR ART)
FIG. 1 is a view of a deconstructed prior art luminaire assembly.
Figure 2:
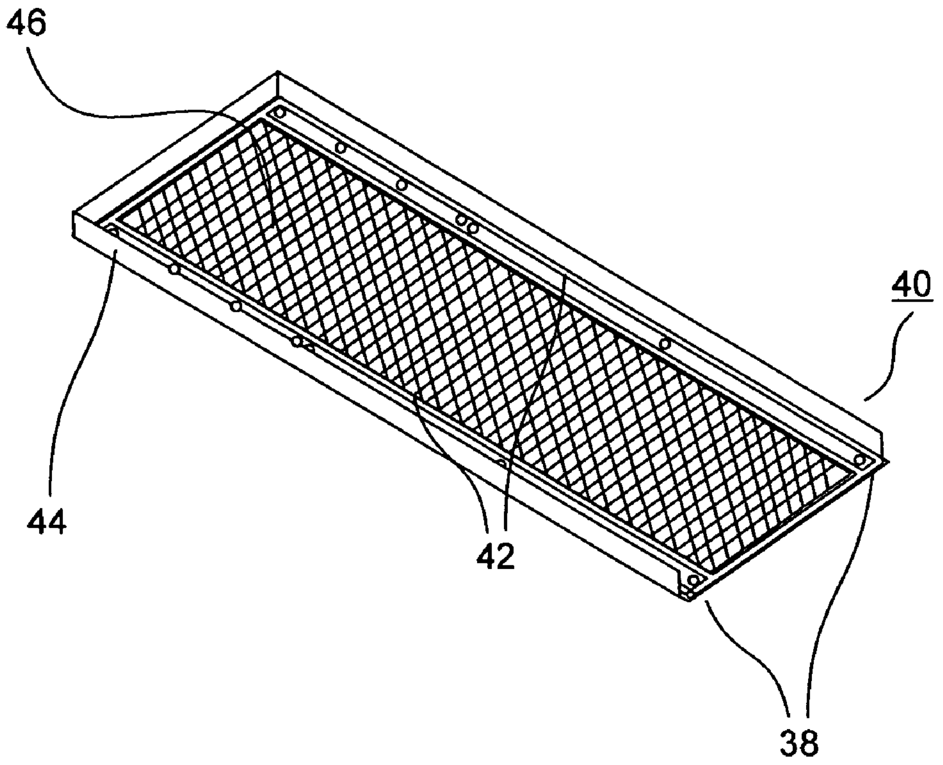
FIG. 2 (PRIOR ART)
FIG. 2 is a prior art RF screen.
Figure 3:
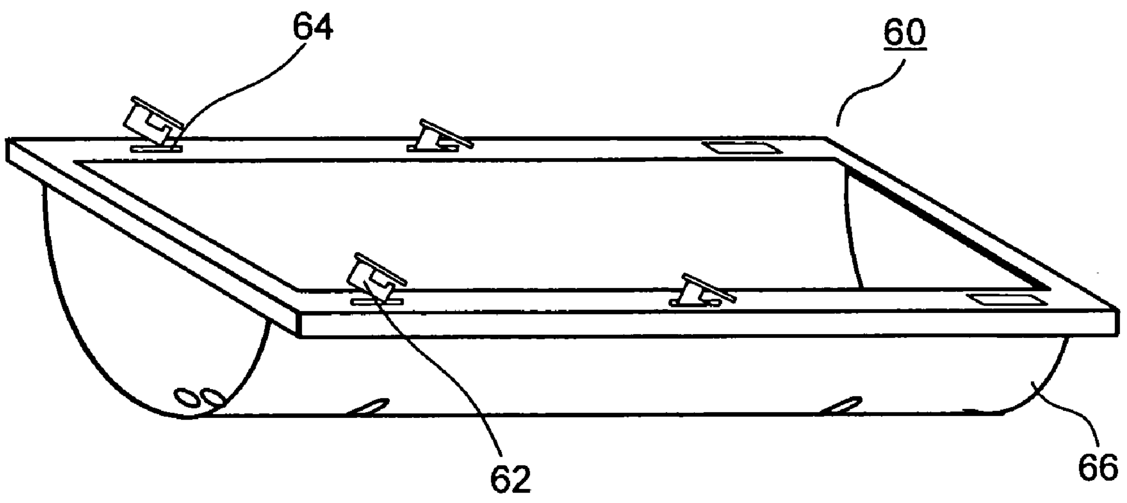
FIG. 3 is a view of an RF screen and main reflector consistent with one embodiment of the present invention.
Figure 4:
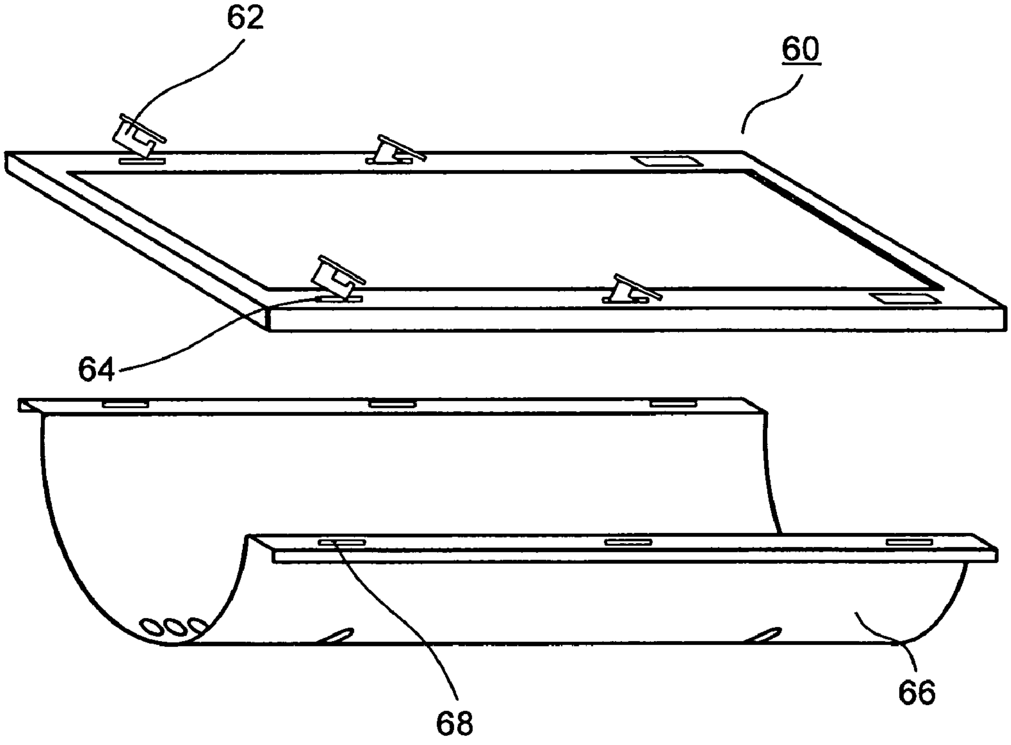
FIG. 4 is a deconstructed view of the RF screen and main reflector consistent with the embodiment of the present invention shown in FIG. 3.

A luminaire assembly with an RF screen assembly and microwave cavity consistent with a first embodiment of the present invention comprises a magnetron (not shown) enclosed in a luminaire assembly housing similar to luminaire assembly housing 20 of FIG. 1. A portion of this first embodiment is consistent with the depiction in FIGS. 3 and 4. The luminaire assembly that accommodates this first embodiment comprises a luminaire assembly housing 20 and a microwave-powered bulb 50. The luminaire assembly further comprises a luminaire reflector assembly, similar to luminaire reflector assembly 30, though suitably modified as discussed below. The luminaire reflector assembly comprises two end reflector bulbs supports similar to end reflector bulb supports 32, two end reflectors similar to end reflectors 34, and microwave coupling slot similar to microwave coupling slot 35. The luminaire reflector assembly further comprises main reflector 66 shown in FIG. 3. Main reflector 66 is similar to main reflector 36, and is configured for attachment to RF screen assembly 60. Main reflector 66 is modified to include latch openings 64 instead of the screw openings 38 of main reflector 36. The luminaire reflector assembly is configured to be mated to the at least one waveguide and to RF screen assembly 60. RF screen assembly 60 comprises a first embodiment reflector latch opening 64, shown in FIG. 4, and a first embodiment latch 62. First embodiment latch 62 comprises a substantially planar region that is larger than latch opening 64. Latch 62 further comprises a substantially hook-shaped region that is configured to pass through latch opening 64 and a second opening 68, and further configured to couple RF screen assembly 60 and main reflector 66. As depicted in FIG. 3, latch 62 couples RF screen assembly 60 and main reflector 66 together, in part, upon rotation about an axis parallel to the plane determined by the face of RF screen assembly 60. Latch 62 is further configured so that it locks in place. As used herein, the term "lock" means that the mechanical energy required to dislodge latch 62 from the configuration of latch 62, latch opening 64, second opening 68, RF screen assembly 60, and main reflector 66, when latch 62 is extended through latch opening 64 and second opening 68 and couples RF screen assembly 60 and main reflector 66 is at an energy minimum.

Figure 5:
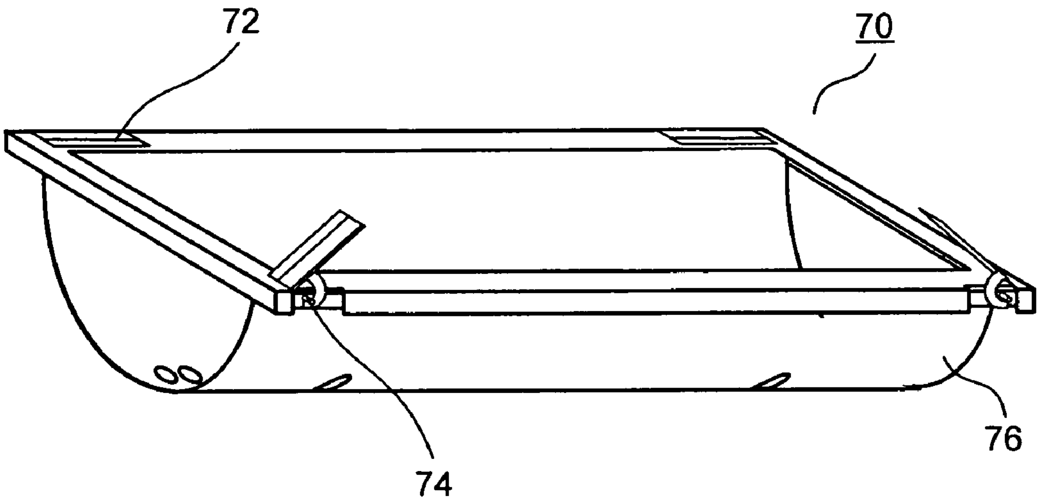
FIG. 5 is a view of an RF screen and main reflector consistent with a second embodiment of the present invention.

A luminaire assembly with an RF screen assembly and microwave cavity consistent with a second embodiment of the present invention comprises a magnetron (not shown) enclosed in a luminaire assembly housing similar to luminaire assembly housing 20 of FIG. 1. A portion of this second embodiment is consistent with the depiction in FIG. 5. The assembly that accommodates this second embodiment comprises a luminaire assembly housing 20 and a microwave-powered bulb 50. The luminaire assembly further comprises a luminaire reflector assembly, similar to luminaire reflector assembly 30, though suitably modified as discussed below. The luminaire reflector assembly comprises two end reflector bulbs supports similar to end reflector bulb supports 32, two end reflectors similar to end reflectors 34, and microwave coupling slot similar to microwave coupling slot 35. The luminaire reflector assembly further comprises main reflector 76 shown in FIG. 5. Main reflector 76 is similar to main reflector 36, and is configured for attachment to RF screen assembly 70. Main reflector 76 is configured to include at least one latch post 74 instead of screw openings 38 of main reflector 36 The luminaire reflector assembly is configured to be mated to at least one waveguide and to RF screen assembly 70 as described below. As seen in FIG. 5, RF screen assembly 70 comprises main reflector 76 with at least one latch post 74 and least one latch 72.

RF screen assembly 70 and the luminaire reflector assembly are configured to form a microwave cavity that can accommodate a microwave-powered bulb that produces radiation which exits the luminaire assembly through the radio-frequency screen mesh material (not shown). At least one latch 72 combines with at least one latch post 74 to create a latching structure. Latch post 74 is configured to extend through at least one opening in RF screen assembly 70. Latch 72 comprises a substantially planar region. Latch 72 and latch post 74 are further configured to couple RF screen assembly 70 and main reflector 76 upon rotation about an axis parallel to the plane determined by the face of RF screen assembly 70. The latch is further designed such that it locks in place. Again, as used herein, the term "lock" means that the mechanical energy required to dislodge latch 72 from the configuration of latch 72, latch post 74, RF screen assembly 70, and main reflector 76, when latch 72 is extended around latch post 74 and couples RF screen assembly 70 and main reflector 76 is at an energy minimum.

Figure 6:
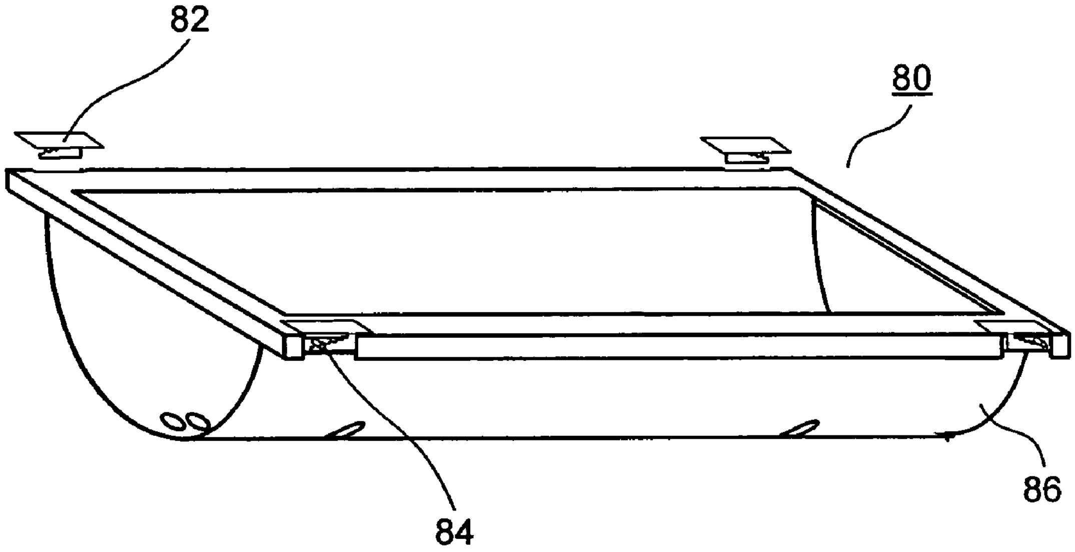
FIG. 6 is a view of an RF screen and main reflector consistent with a third embodiment of the present invention.
Figure 6A:
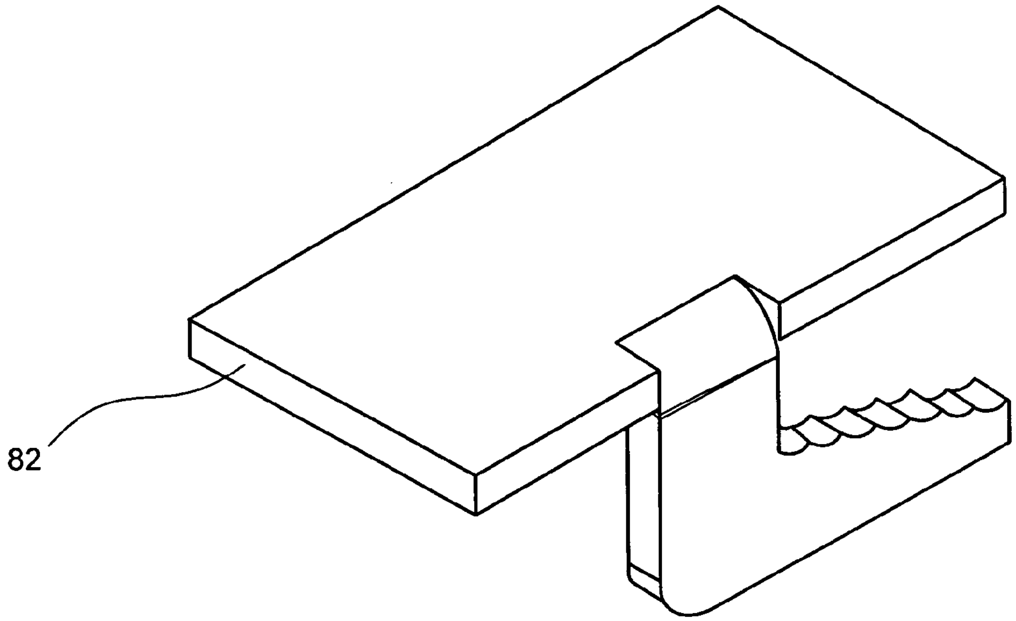
FIG. 6A is a close-up view of a latch from FIG. 6.

A luminaire assembly with an RF screen assembly and microwave cavity consistent with a third embodiment of the present invention comprises a magnetron (not shown) enclosed in a luminaire assembly housing similar to luminaire assembly housing 20 of FIG. 1. A portion of this third embodiment is consistent with the depiction in FIG. 6. The luminaire assembly that accommodates this third embodiment comprises a luminaire assembly housing 20 and a microwave-powered bulb 50. The luminaire assembly further comprises a luminaire reflector assembly, similar to luminaire reflector assembly 30, though suitably modified as discussed below. The luminaire reflector assembly comprises two end reflector bulbs supports similar to end reflector bulb supports 32, two end reflectors similar to end reflectors 34, and microwave coupling slot similar to microwave coupling slot 35. The luminaire reflector assembly further comprises main reflector 86 shown in FIG. 6. Main reflector 86 is similar to main reflector 36, and is configured for attachment to RF screen assembly 80. RF screen assembly 80 is configured to include slots as required by latch 82 instead of the screw openings 38 of RF screen assembly 40. The luminaire reflector assembly is configured to be mated to the at least one waveguide and to RF screen assembly 80 through the use of latch 82. As shown in FIG. 6, RF screen assembly 80 comprises a third embodiment reflector and third embodiment at least one latch post 84 and third embodiment at least one latch 82. An enlarged view of latch 82 can be seen in FIG. 6A. Latch post 84 is configured to extend through the first opening when RF screen assembly 80 and main reflector 86 form the microwave cavity. As shown in FIG. 6A, latch 82 preferably comprises a plurality of curved segments along a wedge-shaped incline. With the curved segments, latch 82 is configured to couple with the at least one latching post 84 and further configured to couple RF screen assembly 80 and main reflector 86 upon translation in a direction parallel to the plane of the RF screen. The latch is further designed such that it locks in place. As used herein, the term "lock" means that the mechanical energy required to dislodge latch 82 from the configuration of latch 82, latch post 84, RF screen assembly 80, and main reflector 86, when latch 82 is extended around latch post 84 and couples RF screen assembly 80 and main reflector 86 is at an energy minimum.

A luminaire assembly with an RF screen assembly and microwave cavity consistent with a fourth embodiment of the present invention comprises a magnetron (not shown) enclosed in a luminaire assembly housing similar to luminaire assembly housing 20 of FIG. 1. A portion of this fourth embodiment is consistent with the depiction in FIG. 7. The assembly that accommodates this fourth embodiment comprises a luminaire assembly housing 20 and a microwave-powered bulb 50. The luminaire assembly further comprises a luminaire reflector assembly, similar to luminaire reflector assembly 30, though suitably modified as discussed below. The luminaire reflector assembly comprises two end reflector bulbs supports similar to end reflector bulb supports 32, two end reflectors similar to end reflectors 34, and microwave coupling slot similar to microwave coupling slot 35. The luminaire reflector assembly further comprises main reflector 96 shown in FIG. 7. Main reflector 96 is similar to main reflector 36, and is configured for attachment to RF screen assembly 90. Cam lock 92 is attached to RF screen assembly 90, and clearance holes are placed in the main reflector 96 to accommodate cam lock 92. The luminaire reflector assembly is configured to be mated to the at least one waveguide and to RF screen assembly 90 through the use of cam lock 92 and cam lock rail 94.

Figure 7:
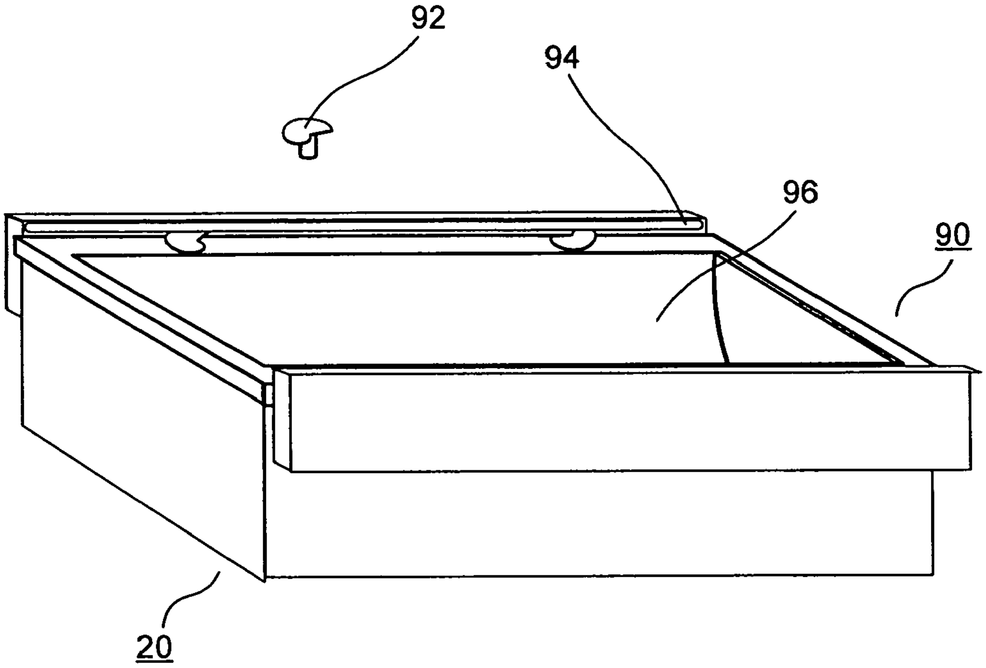
FIG. 7 is a view of an RF screen and luminaire assembly housing consistent with a fourth embodiment of the present invention.

Luminaire assembly 20 of FIG. 7 comprises cam lock rail 94. Luminaire assembly 20 further comprises RF screen assembly 90. RF screen assembly 90 comprises a frame with at least one cam lock 92 attached. Cam lock 92, in combination with RF screen assembly 90, is configured to couple with cam lock rail 94 to exert compressive force on RF screen gasket 42 upon rotation.

A luminaire assembly with an RF screen assembly and microwave cavity consistent with a fifth embodiment of the present invention comprises a magnetron (not shown) enclosed in a luminaire assembly housing similar to luminaire assembly housing 20 of FIG. 1. A portion of this fifth embodiment is consistent with the depiction in FIG. 8. The luminaire assembly that accommodates this fifth embodiment comprises a luminaire assembly housing 20 and a microwave-powered bulb 50. The luminaire assembly further comprises a luminaire reflector assembly, similar to luminaire reflector assembly 30, though suitably modified as discussed below. The luminaire reflector assembly comprises two end reflector bulbs supports similar to end reflector bulb supports 32, two end reflectors similar to end reflectors 34, and microwave coupling slot similar to microwave coupling slot 35. The luminaire reflector assembly further comprises main reflector 36 shown in FIG. 1. The luminaire reflector assembly is configured to be mated to the at least one waveguide and to RF screen assembly 100 through the use of captured fast lead screw 102, as described below.

Figure 8:
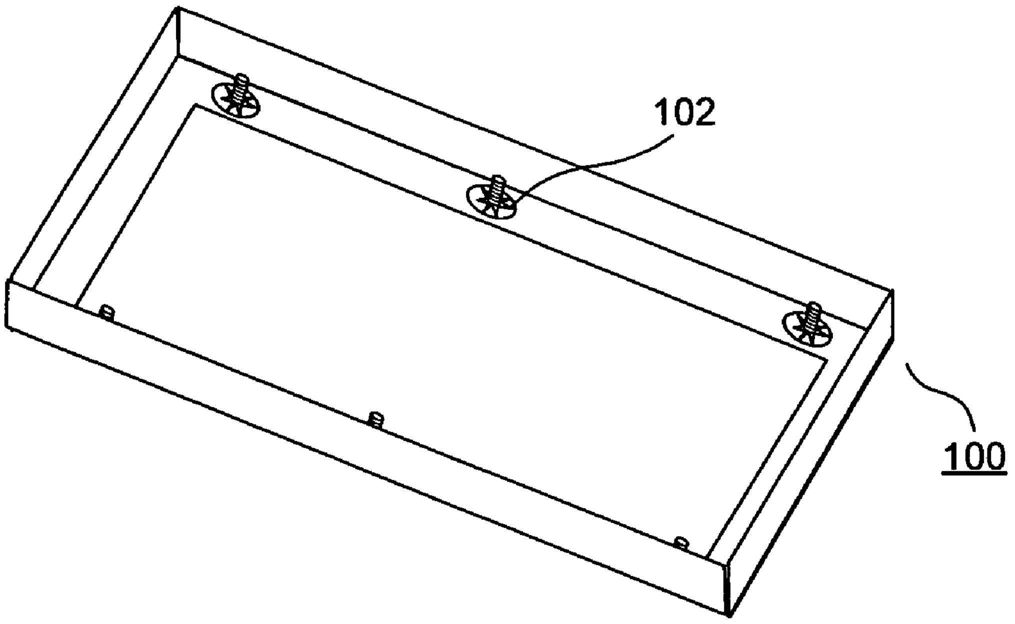
FIG. 8 is a view of an RF screen consistent with a fifth embodiment of the present invention.

Part of the fifth embodiment is shown in FIG. 8. RF screen assembly 100 is configured to be mated to a luminaire reflector. RF screen assembly 100 comprises a frame with at least one captive fast lead screw 102. At least one captive fast lead screw 102 is configured to couple RF screen assembly 100, and the luminaire reflector. The luminaire reflector is modified with fast lead screw threads to accept the fast lead screws. Captive fast lead screw 102 is preferably configured to provide sufficient compressive force with only between 2.5 to 3 turns. In addition, captive fast lead screw 102 is configured to remain attached to RF screen assembly 100 when RF screen assembly 100 is not attached to any reflector.

A luminaire assembly with an RF screen assembly and microwave cavity consistent with a sixth embodiment of the present invention comprises a magnetron (not shown) enclosed in a luminaire assembly housing similar to luminaire assembly housing 20 of FIG. 1. A portion of this sixth embodiment is consistent with the depiction in FIG. 9. The luminaire assembly that accommodates this sixth embodiment comprises a luminaire assembly housing 20 and a microwave-powered bulb 50. The luminaire assembly further comprises a luminaire reflector assembly, similar to luminaire reflector assembly 30, though suitably modified as discussed below. The luminaire reflector assembly comprises two end reflector bulbs supports similar to end reflector bulb supports 32, two end reflectors similar to end reflectors 34, and microwave coupling slot 35. The luminaire reflector assembly further comprises main reflector 116 shown in FIG. 9. Main reflector 116 is similar to main reflector 36, and is configured for the attachment to RF screen assembly 110. The luminaire reflector assembly is configured to be mated to the at least one waveguide and to RF screen 110 through the use of latch 112, as described below.

Figure 9:
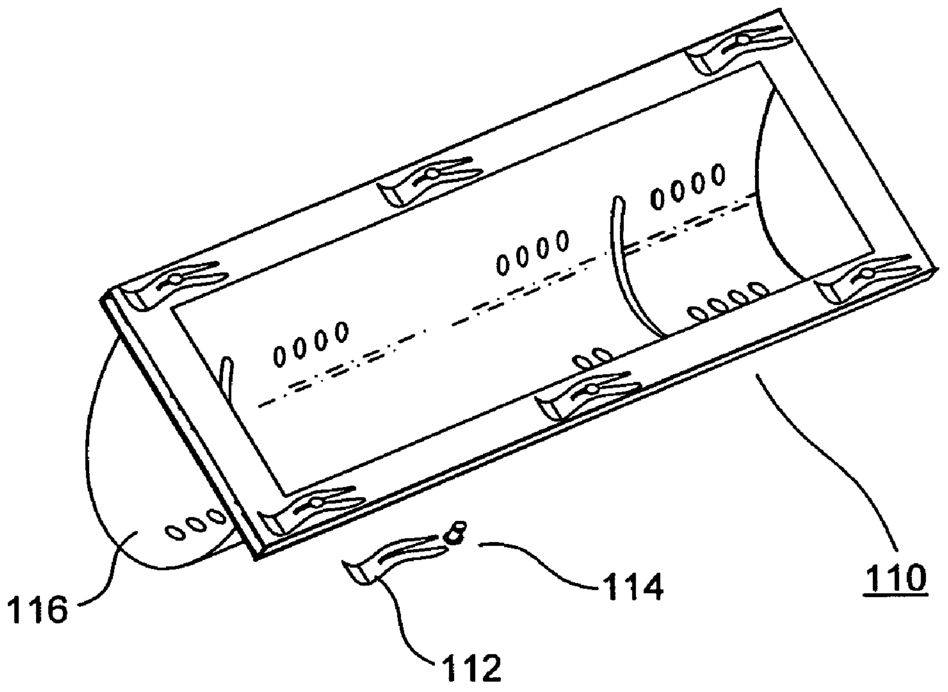
FIG. 9 is a view of an RF screen and main reflector assembly consistent with a sixth embodiment of the present invention.
Figure 10:
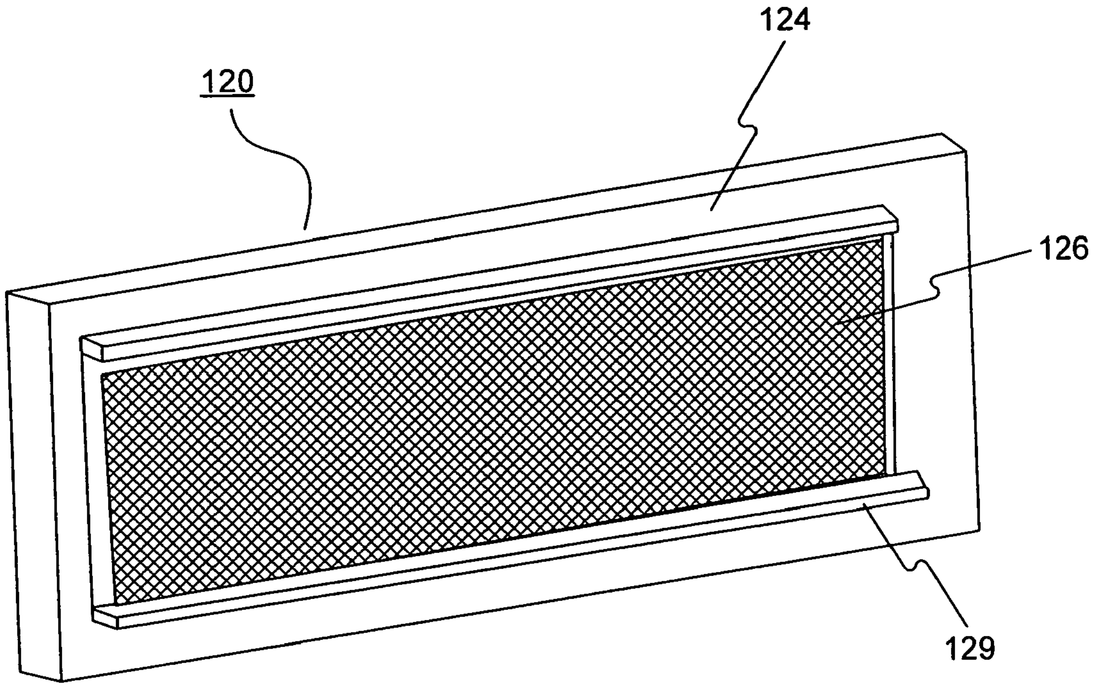
FIG. 10 is a view of an RF screen consistent with a seventh embodiment of the present invention.

RF screen assembly 110 is configured to be mated to luminaire reflector 116. Luminaire reflector 116 comprises at least one latching post 114. Latching post 114 preferably comprises at least two regions. Preferably, one region, the head region, is further away from the reflector assembly than the other region, the body region. Preferably, the head region is wider than the body region. RF screen assembly 110 comprises latch 112. Latch 112 may preferably comprise Tinnerman™ spring clips, or equivalents, that are used to secure RF screen 110 to luminaire reflector 116. Latch 112 is preferably designed so that it is curved and includes a wedge-shaped opening. The wedge-shaped opening is preferably wide enough to allow the body region of latching post 114 to enter the wedge-shaped opening, but too narrow to allow the head region of latching post 114 to pass through the wedge-shaped opening when latch 112 and latching post 114 are engaged as depicted in FIG. 9. In addition, latch 112 is preferably configured with a slight depression around a portion of the wedge-shaped opening so that the head region of latching post 114 settles into the depression when latch 112 and latching post 114 are engaged, or locked, as depicted in FIG. 9. Again, as used herein, the term "lock" means that the mechanical energy required to dislodge latch 112 from the configuration of latch 112, latching post 114, RF screen assembly 110, and luminaire reflector 116, when latch 112 is secured to latching post 114 and couples RF screen assembly 110 and main reflector 116 is at an energy minimum.

In an embodiment of the invention, RF screen gasket 42 (shown in FIG. 1) is a metal mesh gasket attached to an RF screen (e.g. 40, though any of the aforementioned RF screens can be incorporated). RF screen gasket 42 ensures sufficient electrical connections between RF screen 40 and main reflector (e.g. 36, though any of the aforementioned main reflectors can be incorporated). In order to maintain the connection, any one of the aforementioned embodiments of the present invention can be used to secure the RF screen to the main reflector to ensure compression of RF gasket 42.

In a seventh embodiment of another aspect of the invention, an RF screen assembly 120 comprises an RF screen frame 124 and an RF screen mesh material 126. In order to maintain this connection, any one of the aforementioned embodiments of the present invention can be used to secure the RF screen assembly 120 to the main reflector. The RF screen frame 124 defines a plane. The RF screen frame comprises a metal ridge 129 along two sides of an inside opening of the RF screen frame 124. The metal ridge 129 extends in a direction perpendicular to the plane. The metal ridge can prevent a tool, such as a screwdriver, from slipping on the frame and damaging RF screen mesh material 126. In addition, metal ridge 129 provides added rigidity to RF screen frame 124.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A luminaire assembly comprising:

at least one magnetron;

a luminaire reflector with a first region, where the luminaire reflector is configured to be mated to at least one waveguide and to a radio-frequency screen assembly;

a radio frequency gasket with a second region;

the radio-frequency screen assembly comprising a frame with at least a first opening in a third region to accommodate at least one latching structure;

where the radio-frequency screen assembly, the radio frequency gasket, and the luminaire reflector are configured to form a microwave cavity that can accommodate a microwave-powered bulb that produces radiation which exits the luminaire assembly through the radio-frequency screen assembly, and where the first region, the second region, and the third region are configured to be substantially adjacent when the radio-frequency screen assembly, the radio frequency gasket, and the luminaire reflector form the microwave cavity;

where the at least one latching structure is configured to couple the third region of the radio-frequency screen assembly, the second region of the radio frequency gasket, and the first region of the luminaire reflector;

the radio-frequency screen assembly further defining a plane which is substantially perpendicular to the direction of the radiation that exits the luminaire assembly; and where the at least one latching structure is further configured to attach to the combination of the radio-frequency screen assembly, the radio frequency gasket, and the luminaire reflector through a combination of translational motion and rotation where the translational motion includes a component perpendicular to the plane and a component parallel to the plane and the rotation of the latching structure is about an axis that is substantially parallel to the plane; and where the at least one waveguide is configured to couple energy from the at least one magnetron to the microwave-powered bulb.

2. The luminaire assembly of claim 1, where the luminaire reflector is configured with at least one second opening to accommodate the at least one latching structure;

where the latching structure comprises a substantially planar region that is larger than said first opening; and where the latching structure further comprises a substantially hook-shaped region that is configured to pass through said first opening and said second opening and further configured to couple the third region of the radio-frequency screen assembly, the second region of the radio frequency gasket, and the first region of the luminaire reflector upon rotation about the axis substantially parallel to the plane.

3. The luminaire assembly of claim 2;

where the frame of radio-frequency screen assembly comprises an opening for radiation defined by a plurality of edges;

where the radiation produced by the microwave-powered bulb passes through the opening for radiation in the frame of the radio-frequency screen assembly in a first direction;

where the frame comprises a planar portion that is substantially perpendicular to the first direction;

where at least one of the plurality of edges comprises a ridge that extends in a direction perpendicular to, the planar portion and is in the first direction.

4. The luminaire assembly of claim 1, where the luminaire reflector is configured with at least one latching post, where an axis of the latching post parallel to its length is substantially parallel to the axis that is substantially parallel to the plane;

wherein the at least one latching post is configured to extend through the first opening when the radio-frequency screen assembly, the radio frequency gasket, and the luminaire reflector form the microwave cavity;

where the latching structure comprises a substantially planar region; and where the latching structure further comprises a substantially hook-shaped region that is configured to couple with said at least one latching post and further configured to couple the third region of the radio-frequency screen assembly, the second region of the radio frequency gasket, and the first region of the luminaire reflector upon rotation about the axis substantially parallel to the plane.

5. The luminaire assembly of claim 4:

where the frame of radio-frequency screen assembly comprises an opening for radiation defined by a plurality of edges;

where the radiation produced by the microwave-powered bulb passes through the opening for radiation in the frame of the radio-frequency screen assembly in a first direction;

where the frame comprises a planar portion that is substantially perpendicular to the first direction;

where at least one of the plurality of edges comprises a ridge that extends in a direction perpendicular to the planar portion and is in the first direction.

6. The luminaire assembly of claim 1:

where the frame of radio-frequency screen assembly comprises an opening for radiation defined by a plurality of edges;

where the radiation produced by the microwave-powered bulb passes through the opening for radiation in the frame of the radio-frequency screen assembly in a first direction;

where the frame comprises a planar portion that is substantially perpendicular to the first direction;

where at least one of the plurality of edges comprises a ridge that extends in a direction perpendicular to the planar portion and is in the first direction.

7. A luminaire assembly comprising:

at least one magrietron;

a luminaire reflector with a first region, where the luminaire reflector is configured to be mated to at least one waveguide and to a radio-frequency screen assembly;

a radio frequency gasket with a second region;

the radio-frequency screen assembly comprising a frame with at least a first opening in a third region to accommodate at least one latching structure;

where the radio-frequency screen assembly, the radio frequency gasket, and the luminaire reflector are configured to form a microwave cavity that can accommodate a microwave-powered bulb that produces radiation which exits the luminaire assembly through the radio-frequency screen assembly, and where the first region, the second region, and the third region are configured to be substantially adjacent when the radio-frequency screen assembly, the radio frequency gasket, and the luminaire reflector form the microwave cavity;

where the at least one latching structure is configured to couple the third region of the radio-frequency screen assembly, the second region of the radio frequency gasket, and the first region of the luminaire reflector;

the radio-frequency screen assembly further defining a plane which is substantially perpendicular to the direction of the radiation that exits the luminaire assembly; and where the at least one latching structure is further configured to attach to the combination of the radio-frequency screen assembly, the radio frequency gasket, and the luminaire reflector through a combination of translational motion only where the translational motion includes a component parallel to the plane; and where the at least one waveguide is configured to couple energy from the at least one magnetron to the microwave-powered bulb, where the luminaire reflector is configured with at least one latching post, where an axis of the latching post parallel to its length is subsitantially parallel to the plane;

wherein the at least one latching post is configured to extend through the first opening when the radio-frequency screen assembly, the radio frequency gasket, and the luminaire reflector form the microwave cavity;

where the latching structure comprises a substantially planar region; and where the latching structure further comprises a substantially wedge-shaped region that is configured to couple with said at least one latching post and further configured to couple the third region of the radio-frequency screen assembly, the second region of the radio frequency gasket, and the first region of the luminaire reflector upon translation of the latching structure in a direction parallel to the plane.

8. The luminaire assembly of claim 7, where the frame of radio-frequency screen assembly comprises an opening for radiation defined by a plurality of edges;

where the radiation-produced by the microwave-powered bulb passes through the opening for radiation in the frame of the radio-frequency screen assembly in a first direction;

where the frame comprises a planar portion that is substantially perpendicular to the first direction;

where at least one of the plurality of edges comprises a ridge that extends in a direction perpendicular to the planar portion and is in the first direction.

9. A luminaire assembly comprising:

at least one magnetron;

a luminaire reflector with a first region, where the luminaire reflector is configured to be mated to at least one waveguide and to a radio-frequency screen assembly;

a radio frequency gasket with a second region;

the radio-frequency screen assembly'comprising a frame with at least a first opening in a third region to accommodate at least one latching structure;

where the radio-frequency screen assembly, the radio frequency gasket, and the luminaire reflector are configured to form a microwave cavity that can accommodate a microwave-powered bulb that produces radiation which exits the luminaire assembly through the radio-frequency screen assembly, and where the first region, the second region, and the third region are configured to be substantially adjacent when the radio-frequency screen assembly, the radio frequency gasket, and the luminaire reflector form the microwave cavity;

where, the at least one latching structure is configured to couple the third region of the radio-frequency screen assembly, the second region of the radio frequency gasket, and the first region of the luminaire reflector;

the radio-frequency screen assembly further defining a plane which is substantially perpendicular to the direction of the radiation that exits the luminaire assembly; and where the at least one latching structure is further configured to attach to the combination of the radio-frequency screen assembly, the radio frequency gasket, and the luminaire reflector through a combination of translational motion only where the translational motion includes a component parallel to the plane; and where the at least one waveguide is configured to couple energy from the at least one magnetron to the microwave-powered bulb, where the luminaire reflector is configured with at least one latching post, where an axis of the latching post parallel to its length is substantially perpendicular to the plane;

wherein the at least one latching post is configured to extend through the first opening when the radio-frequency screen assembly, the radio frequency gasket, and the luminaire reflector form the microwave cavity;

where the latching structure is substantially curved and includes a substantially wedge-shaped opening that is configured to couple with said at least one latching post and further configured to couple the third region of the radio-frequency screen assembly, the second region of the radio frequency gasket, and the first region of the luminaire reflector upon translation in a direction parallel to the plane.

10. The luminaire assembly of claim 9:

where the frame of radio-frequency screen assembly comprises an opening for radiation defined by a plurality of edges;

where the radiation produced by the microwave-powered bulb passes through the opening for radiation in the frame of the radio-frequency screen assembly in a first direction;

where the frame comprises a planar portion that is substantially perpendicular to the first direction;

where at least one of the plurality of edges comprises a ridge that extends in a direction perpendicular to the planar portion and is in the first direction.

11. A luminaire assembly comprising:

a latching assembly comprising a cam lock rail and at least one cam lock;

at least one magnetron;

a luminaire reflector with a first region, where the luminaire reflector is configured to be mated to at least one waveguide and to a radio-frequency screen assembly;

a radio frequency gasket with a second region;

the radio-frequency screen assembly comprising a frame with at least a first opening in a third region to accommodate the at least one cam lock;

where the radio-frequency screen assembly, the radio frequency gasket, and the luminaire reflector are configured to form a microwave cavity that can accommodate a microwave-powered bulb that produces radiation which exits the luminaire assembly through the radio-frequency screen assembly, and where the first region, the second region, and the third region are configured to be substantially adjacent when the radio-frequency screen assembly, the radio frequency gasket, and the luminaire reflector form the microwave cavity;

where the at least one cam lock in combination with said cam lock rail is configured to couple the third region of the radio-frequency screen assembly, the second region of the radio frequency gasket, and the first region of the luminaire reflector; and where the at least one waveguide is configured to couple energy from the at least one magnetron to the microwave-powered bulb.

12. The luminaire assembly of claim 11:

where the frame of radio-frequency screen assembly comprises an opening for radiation defined by a plurality of edges;

where the radiation produced by the microwave-powered bulb passes through the opening for radiation in the frame of the radio-frequency screen assembly in a first direction;

where the frame comprises a planar portion that is substantially perpendicular to the first direction;

where at least one of the plurality of edges comprises a ridge that extends in a direction perpendicular to the planar portion and is in the first direction.

13. A luminaire assembly comprising:

at least one magnetron;

a luminaire reflector with a first region, where the luminaire reflector is configured to be mated to at least one waveguide and to a radio-frequency screen assembly;

a radio-frequency gasket with a second region;

where the radio-frequency screen assembly comprising a frame with at least one captive fast lead screw;

where the radio-frequency screen assembly, the radio frequency gasket, and the luminaire reflector are configured to form a microwave cavity that can accommodate a microwave-powered bulb that produces radiation which exits the luminaire assembly through the radio-frequency screen assembly, and where the first region, the second region, and a third region are configured to be substantially adjacent when the radio-frequency screen assembly, the radio frequency gasket, and the luminaire reflector form the microwave cavity;

where the at least one captive fast lead screw is configured to couple the third region of the radio-frequency screen assembly, the second region of the radio frequency gasket, and the first region of the luminaire reflector; and where the at least one waveguide is configured to couple energy from the at least one magnetron to the microwave-powered bulb.

14. The luminaire assembly of claim 13:

where the frame of radio-frequency screen assembly comprises an opening for radiation defined by a plurality of edges;

where the radiation produced by the microwave-powered bulb passes through the opening for radiation in the frame of the radio-frequency screen assembly in a first direction;

where the frame comprises a planar portion that is substantially perpendicular to the first direction;

where at least one of the plurality of edges comprises a ridge that extends in a direction perpendicular to the planar portion and is in the first direction.

15. A radio-frequency screen assembly comprising:

a frame;

where the frame comprises an opening for radiation defined by a plurality of edges;

where the radio-frequency screen assembly is configured to form a microwave cavity with a luminaire reflector;

where the microwave cavity is configured to accommodate a microwave-powered bulb that produces radiation which passes through the opening for radiation in the frame of the radio-frequency screen assembly in a first direction;

where the frame comprises a planar portion that is substantially perpendicular to the first direction;

where at least one of the plurality of edges comprises a ridge that extends in a direction perpendicular to the planar portion and is in the first direction.

* * * * *